United States Patent [19]

Förster

[11] 4,058,115
[45] Nov. 15, 1977

[54] METHOD AND APPARATUS FOR EXAMINING HUMAN PERIODONTAL TISSUES

[76] Inventor: Friedrich M. O. Förster, Grathlwohlstrasse 4, D-7410 Reutlingen, Germany

[21] Appl. No.: 628,130

[22] Filed: Nov. 3, 1975

[51] Int. Cl.² .............................................. A61B 5/10
[52] U.S. Cl. ......................................... 128/2 S; 32/1
[58] Field of Search ................ 128/2 R, 2 S, 1.3, 1.4, 128/1.5, 2.06 F, 2.05 T, 2.05 B; 32/1; 73/88.5 R, 12, 11; 33/174 D

[56] References Cited

U.S. PATENT DOCUMENTS

| | | | |
|---|---|---|---|
| 2,492,617 | 12/1949 | Boland et al. | 128/2.06 F |
| 3,070,087 | 12/1962 | Sittel | 128/2 T |
| 3,308,653 | 3/1967 | Roth | 128/2 T |
| 3,420,222 | 1/1969 | Noe et al. | 128/2 S |
| 3,943,913 | 3/1976 | Johnson | 128/2 S |

FOREIGN PATENT DOCUMENTS

| | | | |
|---|---|---|---|
| 143,506 | 1/1961 | U.S.S.R. | 128/2.05 B |

OTHER PUBLICATIONS

Henderson, "American Journal of Physiology", vol. 14, 1905, pp. 287–298.

Primary Examiner—William E. Kamm
Attorney, Agent, or Firm—George J. Netter

[57] ABSTRACT

The force which is to act upon the tooth depends only on the field strength of an applied magnetic field, upon the length and number of the electrical conductors through which the magnetic field passes and upon the current flowing through the conductors. The rigid medium can alter its position relative to the examination head without current added to the area of constant field intensity altering the force. In this manner, it is also possible to achieve good examination results even without complicated, troublesome and expensive creation of a fixed point by means of a mouth insert. The head of the test subject is held still by means of a head or chin support. The transducer head can be alternatively retained in a support or even by hand. With the aid of an electronic function generator, any desired time function for the force acting on the tooth, regardless of whether a sinusoidal, rectangular, stepped or sawtooth increase in force is desired is produced.

18 Claims, 12 Drawing Figures

METHOD AND APPARATUS FOR EXAMINING HUMAN PERIODONTAL TISSUES

The present invention relates to a method and apparatus for examining human periodontal tissues or periodontium, in which a force is exerted on the tooth to be examined and the movement of the tooth resulting from the force is determined, the force being transmitted to the tooth by a rigid medium sliding in a transducer head and the deflection of the tooth is measured.

FIELD OF THE INVENTION

An arrangement of this general type is described in a publication by M. Hofmann entitled "Die Periodontographie des gesunden und erkrankten Parodontiums" (Periodontography of the healthy and the diseased periodontium"), which appeared in the magazine "Deutsche Zahn-, Mund- und Kieferheilkunde", Vol. 48 (1967), published by Johann Ambrosius Barth, Leipzig, Germany. The examinations of the author set forth in this work in which an arrangement of the class indicated above was employed, are now of basic significance in early detection of periodontosis.

Periodontosis in the broad sense is a widespread disease. What is dangerous about degeneration of the periodontium is the fact that in the vast majority of all cases periodontosis is painless, which makes early detection of the disease more difficult. In public mass examinations conducted in the Federal Republic of Germany, it was noted that more than eighty percent (80%) of those examined were suffering from a diseased periodontium. According to comprehensive statistical studies, 25% of juveniles between the ages of 6 and 20, 50% of adults between the ages of 21 and 45, and almost 100% of adults of over 45 years suffer from disease of the periodontium.

The epidemic speed with which periodontium diseases spread and the lack of early warning signs which can be detected by the layman, make methods for simple, fast, early diagnosis, and with quantitative determination of the degeneration if possible, a compelling necessity. All the more so since this widespread disease can be healed quite easily in its early stages.

An important aid in evaluating most types of periodontium diseases is the ability to precisely stipulate the degree to which a tooth can move. Previously, this was usually limited to determining the ultimate amount of the deflection of a tooth under a defined load, which was generally performed only once.

With the above mentioned study, Hofmann for the first time submitted the results of examinations in which the precise deflection of a tooth as a factor of time was determined systematically on a large number of test subjects, while a force which increased over a linear period of time acted on the tooth, and the steepness of the increase in force being uniform in all examinations. The distance/time graphs made from these examinations, called periodontograms by Hofmann, will be discussed in detail in the description of a practical example of this invention, because of the significance of these graphs for understanding and evaluating the invention.

Hofmann employed an electronic displacement transducer, developed at Institut Dr. Forster, in conjunction with a force generator developed by him for measuring the tooth deflection. The displacement transducer is an inductance measuring probe, while the force generator causes the spring energy of a helical spring to increase in a linear manner and to act upon the tooth by means of a synchronous motor and a simple transmission.

While in previous developments the reference point against which the force acted on the tooth and the tooth deflection was measured, was located outside the test subject, so that even the smallest movement of the subject's head affected the results of the measurement, Hofmann fixed the reference point of the teeth of the test subject. This was in the form of a mouth insert designed as a rigid system combining a plurality of groups of teeth, which could be viewed as being immovable in comparison to the tooth to be examined. The mouth insert comprises two impression trays connected rigidly, one with the other, on which the force generator and displacement transducer system was arranged and by which one tray was attached to the teeth of the upper jaw and the other to those of the lower jaw by means of plaster or cold polymerization. If the degree of looseness of the upper front teeth was to be determined, the mouth insert was attached to all lower teeth and to the upper side teeth. In measuring the movability of the lower front teeth, the attachment was vice versa. In this manner, it was possible to eliminate the possibility of the movements of the subject's head affecting the measurement results. However, in the case of examinations of long duration, it was necessary to support the head of the test subject by means of a chin support which was vertically adjustable and could be matched to the size of the test subject.

As mentioned at the outset, because of the widespread nature of degenerative periodontium diseases, a simple, fast diagnostic aid, which can be employed without any major preparatory work is required for early detection of periodontium disease, for evaluating the functional condition and for evaluating the effectiveness of therapeutic measures.

As interesting as the method developed by Hofmann for precise, reproducible measurement of tooth movement has proven to be for an understanding of the mechanisms and processes of physiological and pathological tooth movement, the above described examination arrangement used by him is not suitable for a completely troublefree, fast examination of large segments of the population.

OBJECTS AND SUMMARY

It is, therefore, an object of the present invention to provide an arrangement for examining tooth movement which incorporates only minor or reasonable equipment requirements, on the one hand, permitting fast, simple and dependable examination, on the other, and while providing sufficiently precise results. Moreover, the force required for moving the tooth to be examined should be able to be applied to the tooth in a simple manner and as any desired function of time.

In an arrangement of the type described herein, the force which is to act upon the tooth to be examined depends only on the field strength of an applied magnetic field, upon the length and number of the electrical conductors through which the magnetic field passes and upon the current flowing through the conductors. An additional directing force is not required. The above mentioned rigid medium can alter its position relative to the examination head without current added to the area of constant field intensity altering the force. In this manner, it is also possible to achieve good examination results even without the complicated, troublesome and expensive creation of a fixed point by means of a mouth insert. The head of the test subject can be held still by means of a simple head or chin support. The transducer head can be retained in a simple support or, under some conditions, even by hand.

With the aid of an electronic function generator, any desired time function for the force acting on the tooth, regardless of whether a sinusoidal, rectangular, stepped or sawtooth increase in force is desired is produced.

DESCRIPTION OF PREFERRED EMBODIMENTS

Figure 1:
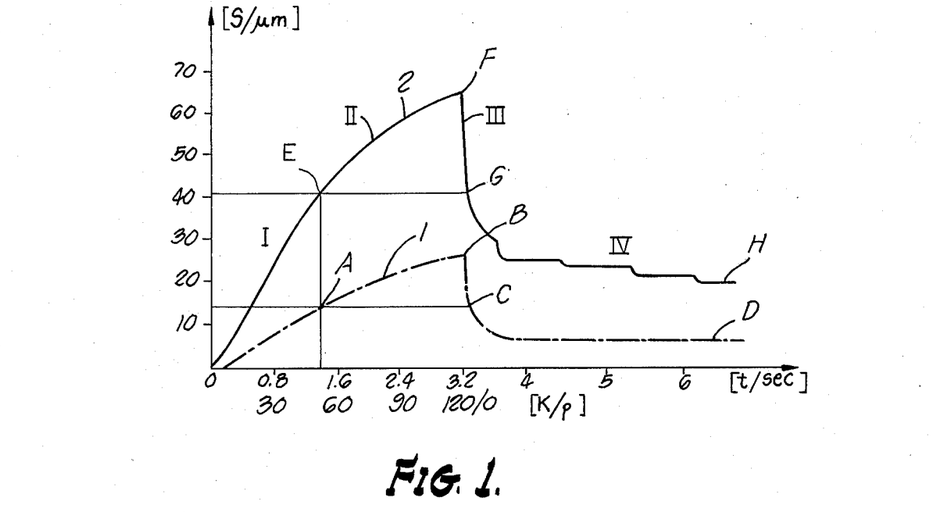
FIG. 1 shows a Hofmann periodontogram.

The Hofmann periodontogram of FIG. 1 shows a comparison of the mean tooth movements of a healthy (dash-dotted line 1) and a diseased (solid line 2) periodontium, in each case with a force in the oral direction increasing in a linear manner as a factor of time, followed by relief of the tooth in question. The Y-axis represents the tooth deflection S in $10^{-6}$ meters ($\mu$m), the X-axis the time $t$ in seconds, and on a further scale the force K acting upon the tooth, indicated in grams of force.

According to Hofmann, the movement of the tooth, which is subjected to a force and then suddenly relieved after 3.2 seconds, occurs in four phases, which are explained by the nature and function of the periodontium and which will now be discussed for the case of a healthy periodontium, as shown in dash-dotted line 1 of FIG. 1.

During phase I, the initial or interperiodontal phase corresponding to distance O - A, under the influence of force K the fibrillae bundles of the periodontium, which are only slightly aligned and wavy in their position of rest, stretch and a displacement of fluid simultaneously takes place.

Phase II, the periodontal phase, corresponds to distance A - B. Under the influence of the increasing force, the collagenic fibrillae within the fiber bundles stiffen and become tense, which is followed by a tensile strain of the hard tissue.

Phase III commences with the sudden elimination of force K after the maximum force amplitude has been reached, in this case 120 grams, and extends for the distance B - C.

The rapid return to approximately 45% of the tooth deflection in about 1/20 of a second represents the relief of the bundles of fibers which were tensioned in phase II.

Phase III can be differentiated from phase IV, in which the fibers slowly return to their original position, by the point of reversal C, where the decline, which is almost a straight line immediately after elimination of the force, becomes curved.

During the slow return movement along line C - D in phase IV, which can take up to several minutes, the tooth slowly but surely approaches its initial position. During this phase, the fiber bundles again return to their unaligned, wavy initial position, while the interperiodontal fluid displacement which occurred in phase I is eliminated through hydrostatic pressure compensation.

In developing methods for evaluating the functional condition of the periodontium, for objective evaluation of various therapies, and finally for early detection of a disease, it is necessary to deal with those phenomena which produce the most significant possible differences, depending upon whether the behaviour of the periodontium is physiological or pathological.

For this reason, the curve of movement of a healthy tooth when subjected to a force and then relieved, i.e., physiological tooth movement 1, is compared with pathological tooth movement 2 with a diseased periodontium.

During phase I (distance O - E) the pathologically damaged periodontium displays a significantly greater initial deflection than the healthy periodontium. In comparing the mean oral tooth movement, at point E, the end of the initial phase, the tooth of the diseased periodontium shows a deflection which is 2.8 times greater than that of the tooth of the healthy periodontium (point A).

In periodontal phase II (distance E - F), as well the mean deflection of the diseased periodontium is approximately twice as steep as that of the healthy periodontium, however, the difference in graph steepness of the tooth movement between the diseased and the healthy periodontium is significantly less in phase II than in initial phase I.

During phase III (distance F - G), a difference in the rapid return cannot be observed between the diseased and the healthy periodontium because of the limitation of the equipment employed (insufficient speed of registration).

On the other hand, during phase IV (distance G - H), it is possible to observe an especially significant phenomenon in the diseased periodontium as opposed to a healthy periodontium: The return to the initial position occurs in periodic steps, whose frequency corresponds to the pulse frequency. These pulsating movements occur as a common symptom of all diseases of the periodontium studied by Hofmann, even — and this is of particular importance — in those cases in which the magnitude of the deflection of the tooth according to FIG. 1 extended into the spectrum of variation of tooth deflection of a healthy periodontium. Hofmann, therefore, considers these pulsating movements of the tooth during slow return of phase IV to be an early symptom of the commencement of an inflammatory alteration of the periodontium.

The tooth movements under the influence of a vestibular direction of force, which were also studied by Hofmann, produce a basically similar picture after being evaluated as vestibular periodontograms. However, in this case the differences between the healthy and the diseased peridontium are not nearly as clear as is the case with oral periodontograms.

According to FIG. 1, with a linear increase in force the tooth movement extends through initial phase I and then through peridontal phase II. In this connection, it is amazing, and this observation can only be explained through the specially selected velocity of the increase in force, that the steepness dS/dK of tooth deflection S with force K does not differ more greatly in phases I and II, even through the mechanisms of the occurrences in phases I and II are largely different.

In phase I, tension free ordering processes, alignment of the wavy fibrillae bundles as well as interperiodontal fluid displacement takes place, none of which is capable of storing significant potential energy. During phase I, there is no "tensioning of a spring", rather the force to be applied is consumed irreversibly in the friction to be overcome.

Phase II, on the other hand, displays all signs of an elastic tensioning of the collagenic fibrillae, which is followed by an elastic deformation of the hard tissue. In phase II, the consumed deformation work is largely stored as a product of force and distance.

The completely different physical mechanisms upon which phases I and II are based can be seen much better during relief phases III and IV. In this case, the tooth movement occurring in 1/20 second can be clearly explained as consumption of the stored elastic energy, while points of reversal C and G can clearly be seen to be the transition to a creep zone.

From what has been said above, it can be seen that during phase I the tooth movement must react significantly more sensitively to alterations in the velocity of the increase of force than in phase II. The higher the selected velocity of increase of force acting on the tooth, the more the tooth will resist deflection in phase I, as there is not enough time for tension free alignment of the wavy fibrillae bundles and for interperiodontal fluid displacement. It is, therefore, possible to assume that due to the largely differing mechanisms of force conversion in phases I and II, a greatly differing behaviour must result in the two phases if the tooth is caused to move back and forth by a periodically acting force instead of the previous, quasi-static force increasing linearly as a factor of time. In this connection, the periodic deflection can take place either about the the position of rest of the tooth or can be superimposed over a deflection provided by an additional static force.

Figure 2:
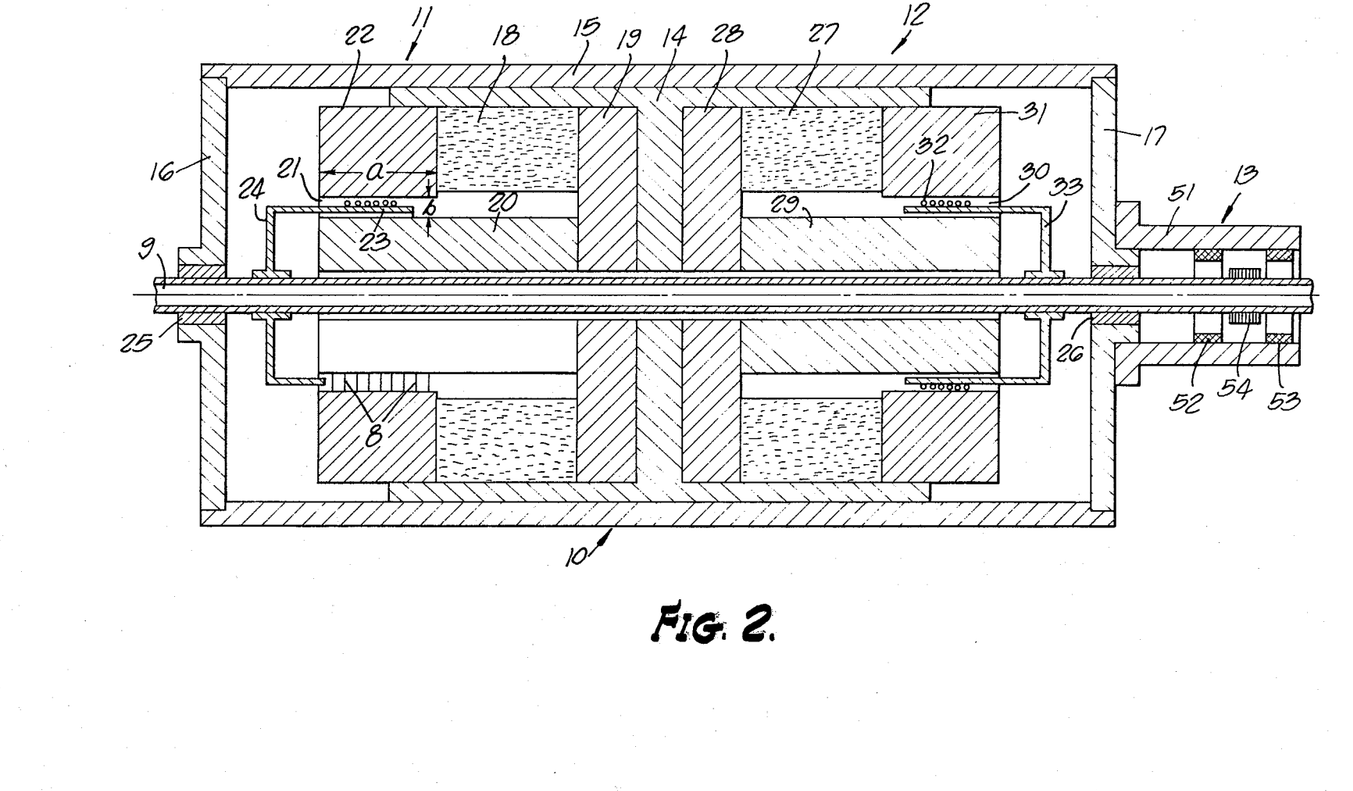
FIG. 2 shows a sectional elevational view of a transducer head.

The arrangement shown as a section in FIG. 2 offers the ability to apply both a static and a periodically acting alternating force to the tooth. The above mentioned forces can be applied independently in differing strengths, dependent only upon the electric currents fed into the arrangement, and independently of the location of the force and of the medium transmitting the deflection.

Transducer head 10 generally comprises a displacement generator 11, a dynamic displacement pickup 12 also integrated into the transducer head, and a static displacement pickup 13 flanged on the outside. The link between transducer head 10 and the tooth to be examined, designated as a rigid member at the outset, is a thin, sturdy tube 9 in this case. The stationary members of froce generator 11 and displacement pickup 12 are retained together in each case in a mounting bushing 14, which in turn is installed in a cylindrical housing 15 having lids 16 and 17.

A magnetic circuit formed by the stationary members of force generator 11 comprises an annular permanent magnet 18, a soft iron disc 19 with centralized hole, a soft iron core 20 which also has a bore, an air gap 21, and an annular pole shoe 22. In air gap 21 there is a high magnetic flux 8 with radial lines of force, whose consistancy can be termed good throughout almost the entire length of the air gap up to a point approximately one half of the gap width $b/2$ from the other end of the gap. Arranged in air gap 21 is a coil 23 of conductor wire wound onto an annular member 24 which is rigidly attached to tube 9. Movements of coil 23 are transmitted to the tooth to be examined by means of annular member 24 and tube 9, the latter being mounted in bearings 25 and 26.

In this connection, a few words should also be said regarding bearings 25 and 26, which serve to permit longitudinal sliding movement of tube 9 with as little friction as possible. In the simplest case, plain plastic thrust bearings of special quality can be selected, however it is generally advisable to employ precision ball bearings. For extreme demands, the employment of air cushion bearings may be necessary. However, it is practical for air cushion bearings not to be employed outside on lids 16, 17, but to extend within the holes through soft iron members 19, 20, 28 and 29 in order to ensure a wide air cushion. Good alignment of bearings 25, 26 is important no matter which bearing method is employed.

The force K occurring in the coil is determined in accordance with the following mathematical formula:

$$K = 0.32 \; 10^{-3} (n)(D)(I)(H) \text{ (grams)} \tag{1}$$

where $n$ is the number of coil windings, $D$ is the coil diameter in centimeters, $I$ is the current in amperes and $H$ is the gap field intensity in Oersteds. For example, if the number of windings is $n = 100$, there is a current of 100 milliamperes, a field intensity of 10,000 Oersteds and a coil diameter of 3.8 centimeters (according to FIG. 2), this results in a force of 121 grams, i.e., the maximum force employed in Hofmann's experiments. The force acting upon the tooth can easily be determined by metering the current. Moreover, with the given data for field intensity and coil diameter, the number of windings can be selected in such a manner that force K of the force generator in grams can coincide precisely with the current $I$ in milliamperes, so that a good milliammeter can be employed as a calibrated dynamometer.

Since the field intensity in air gap 21 is constant almost to the end of the gap, the force acting upon the tooth to be examined in this area is independent of axial displacements of coil 23 and tube 9. As opposed to previously employed force generators, a minor change in the position of the test subject relative to the force generator does not affect the force acting upon the tooth to be examined. Thus, the conventional necessity of applying the force by means of reference points fixed to the teeth is not normally required.

The object of the dynamic displacement pickup is to precisely reproduce the movements of the tooth to be examined in the form of an electrical signal, independently of the chance initial position of the tooth at the beginning of the movements. For this reason, displacement pickup 12 and force generator 11 are connected with the tooth by means of the same rigid member, tube 9, and, with the exception of the number of coil windings, are of identical design.

In the same manner as displacement generator 11, displacement pickup 12 has a magnetic circuit comprising a permanent magnet 27, a soft iron disc 28, a soft iron core 29, an air gap 30 and a pole shoe 31. In air gap 30, a coil 32 having a large number of windings is wound onto an annular member 33 which is rigidly attached to tube 9.

Figure 3:
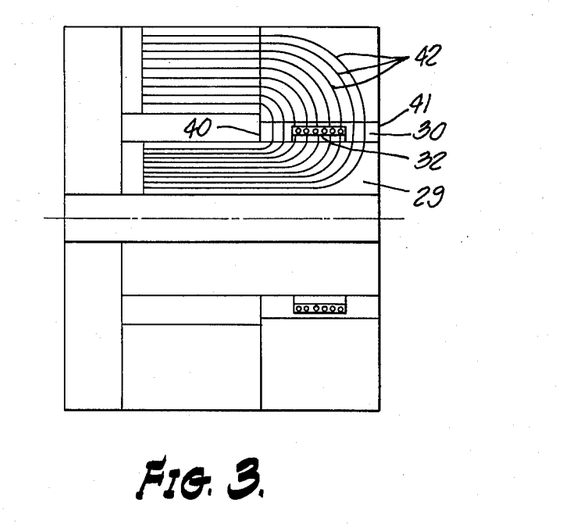
FIG. 3 shows the lines of flux in the magnetic circuit of the transducer head of FIG. 2.

Here again, the important factor is the uniformity of the lines of force 42, which extend to almost the ends 40 and 41 of the gap; the lines of force 42 are shown separately again in FIG. 3. The number of lines of force in soft iron core 29 declines precisely per unit of distance as measured in the direction away from end 41 of the gap, in the amount that lines of force extend into the air gap per unit of distance. However, since the field intensity in the air gap is constant until a point almost at the end of the gap, the decline in density of the lines of force per unit of distance in the soft iron core 29 must be almost constant throughout the entire length of the gap. According to the law of induction, the movement of a coil in a magnetic field induces an electrical voltage at its terminals whose magnitude corresponds to the velocity of alteration of the magnetic flux surrounded by the coil. From what has been said above, it can be seen that the same electrical voltages will also result with the same deflections if coil 32 is moved axially in air gap 30, independently of the chance initial position of the coil. In the case of periodic movements, the amount of this voltage is obtainable from the following formula:

$$E = 19.47 \, (n) \, (f) \, (D) \, (A) \, (H) \times 10^{-8} \text{(volts)} \quad (2)$$

wherein $n$ is the number of coil windings, $f$ is the frequency of the movement, $D$ is the diameter of soft iron core 29 in centimeters, $A$ is the deflection of the coil in centimeters and $H$ is the fluid intensity in Oersteds. In an assumed example where $n = 1,000$ turns, $f = 5$Hz, $D = 3.8$ cm., $A = 1$ $\mu$m $= 10^{-4}$ cm and $H = 10,000$ Oe, a voltage of $E = 3.7$ millivolts will result. A voltage of this magnitude can still be metered without interference with a high degree of accuracy. Thus, in the case of periodic tooth movements displacement pickup 12 proves to be suitable for the resolution of tooth deflections of less than 1 $\mu$m.

In many cases, in addition to the above described dynamic displacement pickup 12, a static displacement pickup 13 may also appear to be desirable. According to FIG. 2, a static displacement pickup of this type is installed in a cylindrical transducer housing 51, which is flanged to lid 17. Two coils 52 and 53, connected electrically to form a half bridge, are installed in housing 51 at a given axial distance one from the other. A highly magnetically permeable material 54 is attached in the middle between coils 52 and 53 as well as coaxially thereto on tube 9.

Figure 4:
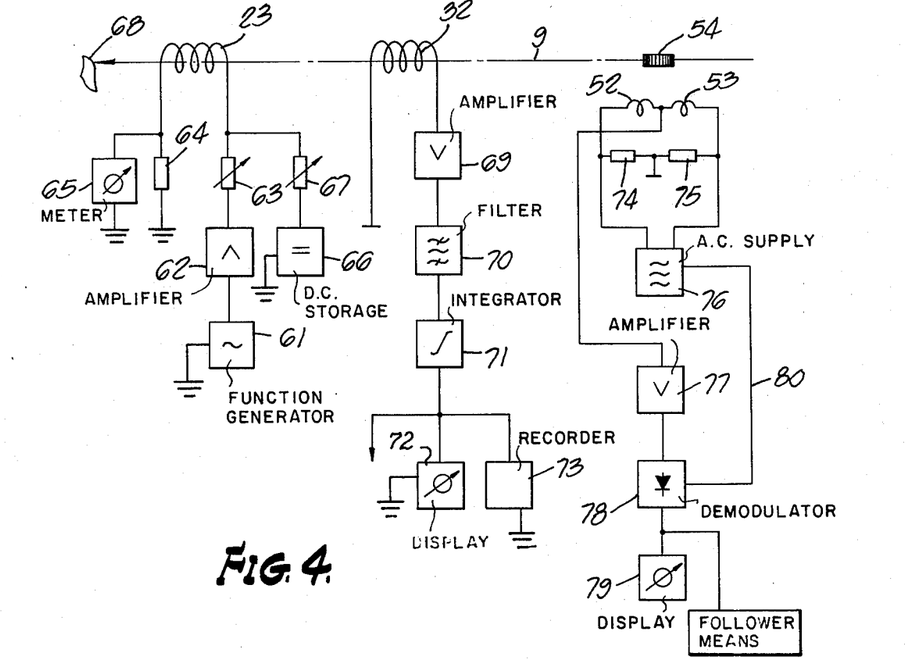
FIG. 4 shows a schematic circuit diagram for the employment of the transducer head of FIG. 2.

FIG. 4 shows a simplified schematic representation of a possible embodiment of the electrical circuit for the above described transducer system. In this representation, 61 is a function generator, which can give off electrical A. C. voltages of varying duration. By means of a power amplifier 62 and an adjustable resistor 63, with whose aid the current amplitude can be selected, a current is sent through force generator coil 23 and a small series resistor 64. The latter serves to generate a voltage drop which is proportional to the coil current, with the voltage drop being able to read by means of a meter 65. A D. C. supply 66 permits a D. C. coil voltage to superimpose the A. C. coil voltage by means of the adjustable resistor 67. In this manner, it is possible to have both an alternating force and a static force act on tooth 68 simultaneously, whereby the intensity of each force can be stipulated separately.

The voltage of displacement pickup coil 32 is amplified by amplifier 69 and travels through a filter stage 70 and an integrator 71 to a display 72, a recorder 73 and/or any other evaluation means. Filter stage 70 serves to suppress interfering external signals located outside the range of the generator frequency, which could be caused by movements of the test subject's head, for example. Integrator 71 converts the velocity proportional voltage of the displacement pickup into a distance proportional voltage. In the case of tooth movements with a changeable frequency of function generator 61, integrator 71 also makes the influence of the frequency on the tooth deflection display more pronounced.

The two coils 52 and 53 are connected to form a bridge with resistors 74 and 75, the bridge supplied with a frequency of 100kHz, for example, for a high frequency voltage supply 76. The output voltage of the bridge is supplied to a display 79, or any other evaluation stage, via an amplifier 77 and a demodulator 78 which is controlled from the bridge supply voltage by means of control lead 80. The bridge is in balance when core 54 is precisely centered between coils 52 and 53. Core 54 is fixed in such a manner that it assumes the position of balance when force generator coil 23, as well as displacement pickup coil 32, are centered in the uniform magnetic field area of the respective air gap. Thus, there is a signal voltage at the output of demodulator 78; this voltage is zero in the indicated center position of coils 23 and 32 or is proportional to the amount of positive or negative deviation if the coils deviate from the center position. While the indication of this signal voltage by display 79 permits remote monitoring of the center position of the transducer coils, it is also possible to utilize this signal voltage for controlling follower means for automatically locating the transducer head in the desired center position.

Figures 5, 8:
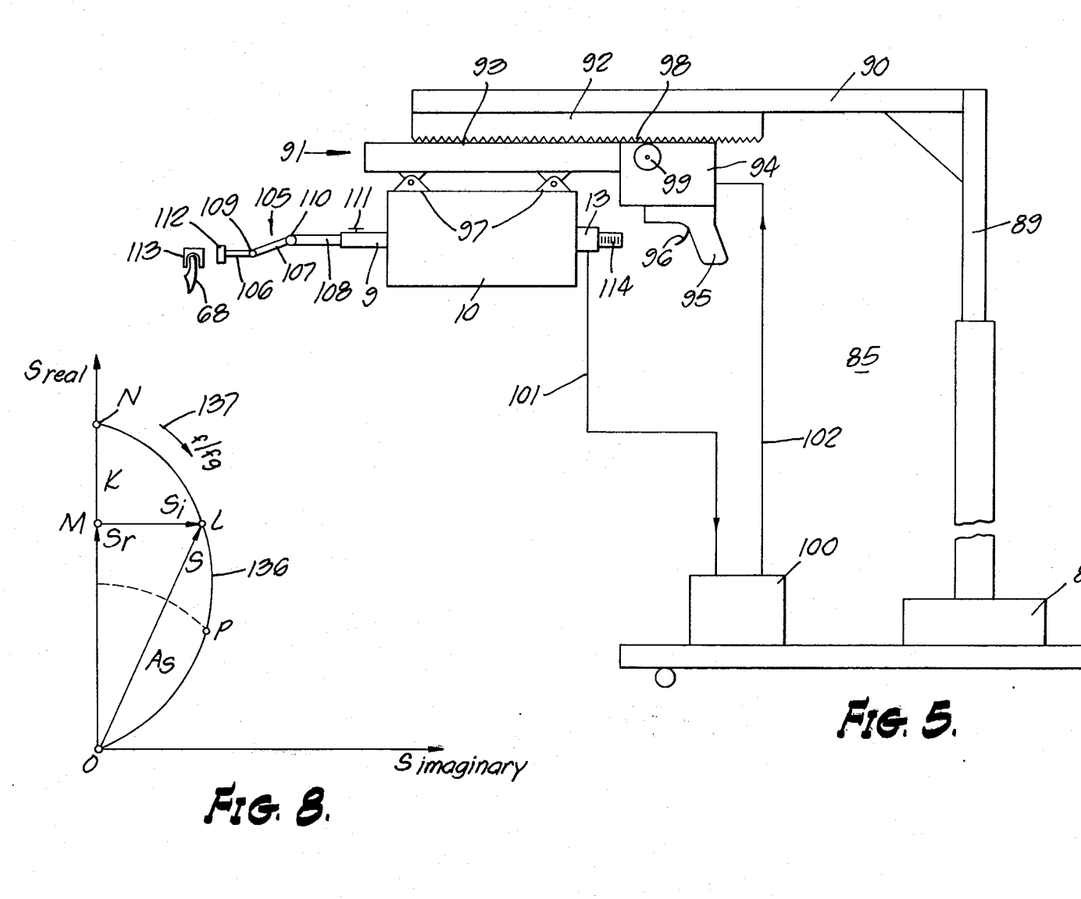
FIG. 5 shows a transducer head suspension system.
FIG. 8 shows a hodograph of the tooth movement.

FIG. 5 shows a stand 85, from which is suspended a transducer head 10, with follower means of this type being provided. Stand 85 comprises a mobile base 86 with wheels 87, a pedestal 88 attached thereon, a pivotable and vertically adjustable telescopic guide 89, a beam 90 attached thereto, and horizontal adjustment means 91 supported by beam 90. The horizontal adjustment means 91 has a horizontal guide 92, through which there are connected with beam 90 a slide 93 slidably suspended in horizontal guide 92, as well as a drive member 94 with handle 95 and trigger 96. Transducer head 10 is attached to slide 93 by means of brackets 97. The bottom of horizontal guide 92 has a tooth rack 98 which meshes with a pinion 99, and which can be caused to rotate by a servo-motor arranged in drive member 94. Also provided is a follower amplifier 100 which is connected with static displacement pickup 13 and the servo-motor of drive member 94 by means of leads 101 and 102.

Tube 9, which slides freely in transducer head 10, is coupled to tooth 68 by means of a linkage 105 having elements 106, 107 and 108 and ball-and-socket joints 109 and 110. Element 108 is adjustably guided in tube 9 and can be fixed by means of a setscrew 111. The tip of element 106 carries an attacting magnet 112. The connection between tooth 68 and attracting magnet 112 can be provided by means of caps 113 of ferromagnetic material bent into a U-shape, which are attached to tooth 68 by means of a fast-drying fixing agent. The position of tube 9 in transducer head 10 can be monitored directly on a scale 114.

To put the transducer system according to FIG. 5 into service, cap 113 is first attached in a suitable manner to tooth 68 to be examined. Base 86 is rolled to a position in the vicinity of the test subject and wheels 87 are then arrested. Transducer head 10 and linkage 105 are then positioned near tooth 68 by swivelling beam 90, vertically adjusting telescopic guide 89 and they are stopped in this position. Using handle 95, the slide is then moved toward the test subject, while simultaneously making sure that the side of cap 113 and the contact surface of attracting magnet 112 are kept parallel by means of ball-and-socket joints 109 and 110. When the two above mentioned surfaces contact, a rigid connection is provided between tooth 68 and linkage 105; this connection can be subjected to a tensile strain of several hundred grams force, yet can be released in a simple manner again by sliding attracting magnet 112 laterally. After this connection has been made, the follower means are put into operation temporarily by actuating trigger 96. Follower amplifier 100 supplies current to the servo-motor, thereby moving the transducer head relative to tube 9 by means of rack 98 and pinion 99, until the desired center position of coils 23 and 32 in the respective air gaps 21 and 30 has been reached. The follower means are switched off by releasing trigger 96. After arresting ball-and-socket joints 109 and 110, and horizontal adjustment means 91, the arrangement is ready to perform examinations. If increased resiliency of linkage 105 relative to tipping movements of tooth 68 during its deflection is required, one of the ball-and-socket joints 109, 110 can remain movable.

Of course, it is also possible to operate the arrangement without the amenity of an automatic follower means. In this case, the center position of coils 23, 32 is set according to scale 114 and setscrew 111 is loosened. Transducer head 10 and linkage 105 are then moved toward tooth 68 by means of slide 93 until the attracting magnet attracts. After tightening setscrew 111 and arresting ball-and-socket joints 109 and 110, as well as horizontal adjustment means 91, the arrangement is ready to perfrom examinations. If necessary, means for providing automatic fine displacement of the transducer head suspension means can also be employed in place of the automatic follower means.

In the arrangement described above, the provision of a fixed reference point on the test subject during the examination of the tooth movement with periodic force was intentionally eliminated in the interest of being able to perform fast mass examinations. On the contrary, it is sufficient for the head of the test subject to be kept still and supported at the chin during the examination. As already suggested above, slight, unavoidable movement amplitudes of the head can be eliminated from the results by appropriately filtering the electronic signal.

Figure 6:
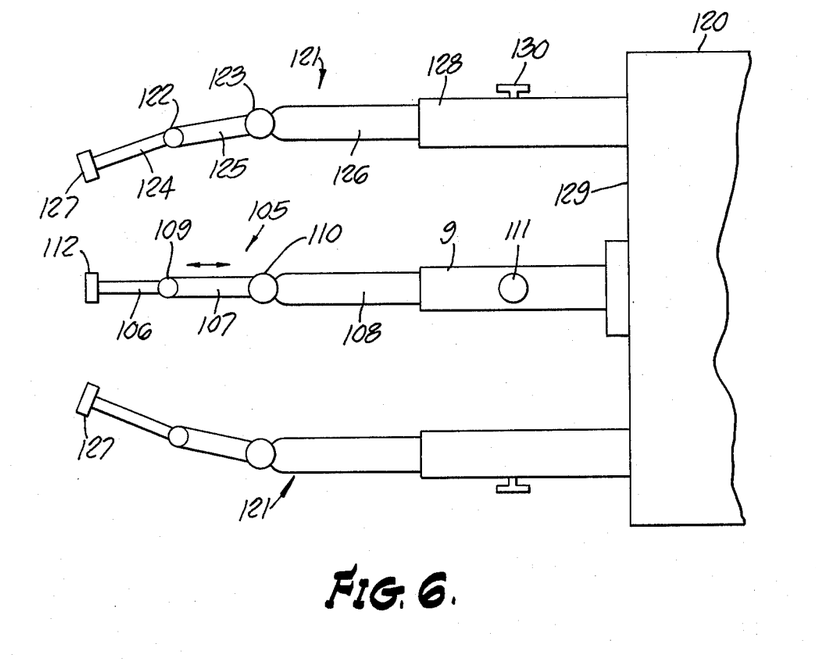
FIG. 6 shows a support means on the transducer head.

In addition, a simple technique for fixing the transducer system to the teeth will now be described for those cases where it is desired, e.g. for measuring the movement of a tooth with one single application of force. FIG. 6 shows a top view of a transducer head 120 which was modified for this purpose. Tube 9 with linkage 105 for coupling the force to the tooth to be examined can be basically identical with the corresponding items described above. However, there are also two supports 121 attached to the housing of the transducer head next to tube 9. In a similar manner as in linkage 105, these supports 121 have three elements 124, 125 and 126, connected one with the other by means of ball-and-socket joints 122 and 123. The tip of element 124 carries a magnet 127. Element 126 is slidably connected with tube 128, which is attached to the front of housing lid 129, and can be fixed by means of a setscrew 130. Magnets 127 serve for coupling supports 121 to teeth or groups of teeth which are located lateral to the tooth to be examined with the aid of ferromagnetic, U-shaped caps, which are connected to the tooth or group of teeth by means of a fast drying fixing agent.

Figure 7:
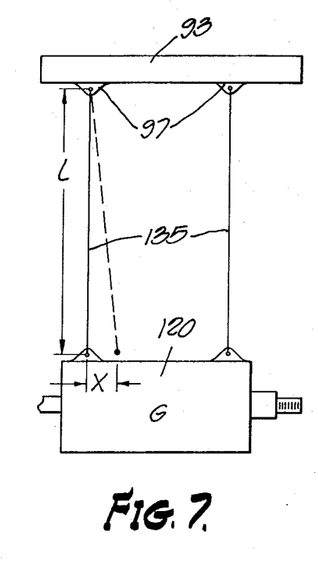
FIG. 7 shows a modified transducer head suspension system.

Transducer head 120 is suspended from a stand, modified slightly from stand 85 according to FIG. 5, of which only slide 93 of horizontal guide means 91 is indicated in FIG. 7. Transducer head 120 is suspended from brackets 97 of slide 93 by means of two (or preferably four) cables 135. If the suspended transducer system is viewed as being a pendulum having a length $l$ in cm and a weight $G$ in grams, the force $K$ with which support means 121 contact the teeth for small deflections $x$ in cm can be indicated approximately through the following simple formula:

$$K \simeq G \cdot x/l \tag{3}$$

An example will indicate the magnitude of this force. A weight $G$ of 2 kg and a length $l$ of 100 cm results in an increase in force of 20 grams per cm of deflection $x$.

If support means 121 have already been fixed without tension of first placing magnets 127 in a contacting relationship with the ferromagnetic tooth caps by setscrews 130, it is possible to set any desired contacting force of support means 121 on the teeth by merely shifting slide 93 a defined distance $x$.

The following will show that a method of examining tooth movement which utilized an arrangement according to FIG. 5 with periodic force is capable of providing a number of important items of tooth information which characterize the test subject.

In Hofmann's periodontograms with quasi-static tooth deflection, the entire tooth deflection curve is used for the diagnosis. It would undoubtedly be of significant advantage if pathological behaviour of the periodontium in its variance from the physiological behaviour were indicated by fundamental figures.

The introduction of the complex tooth movement plane, which indicates the real tooth movement on the Y-axis and imaginary components on the X-axis, is employed for this purpose. With defined test conditions, each tooth is represented by a vector, or a point forming the peak of this vector, in the complex tooth movement plane.

The tooth being subjected to the alternating force lags behind this alternating force with a delay. There is generally a so-called relaxation effect in the periodic tooth movement i.e., a lag between the force and the movement of the tooth, as internal resistances (in particular frictional effects during phase I of the periodontograms) result in a delay in termination of the tooth deflection corresponding to the force. The period of time required until a new tooth deflection balance has been reached after a given force has been applied to the tooth, i.e., the ultimate value of the tooth deflection which corresponds to the respective force, is termed the relaxation time.

As can be seen from the periodontogram according to FIG. 1, the relaxation times in phases I and II must differ by several magnitudes. This can be seen especially clearly during tooth relief phases III and IV. If the force of the force generator acts upon the tooth periodically, this lag in tooth deflection behind the respective value of force at any given moment will result in phase shifting between the force and the tooth deflection. The periodic tooth deflection lags behind the periodic force applied to the tooth. Only with an infinitely slow frequency, i.e., where the frequency of the force acting upon the tooth is 0, will there be no lag between the application of the force and the tooth deflection, i.e., will there be no phase shifting.

If a periodic force with a force amplitude of $A_K$ and a frequency of $f$ is applied to the tooth, the force $K(t)$ can be calculated as a function of time as follows:

$$K(t) = A_K \sin 2\pi f t \qquad (4)$$

The tooth deflection S responsive to this periodic force is represented by the following movement equation:

$$S(t) = A_S \sin (2\pi f t - \phi) \qquad (5)$$

This means that a frequency of $f$ and a force amplitude of $A_K$ will result in a tooth movement amplitude of $S$, which lags behind the force by phase angle $\phi$.

FIG. 8, which represents the complex tooth movement plane, shows both vector S of tooth movement and vector K of force. Distance O - L represents the amplitude $A_S$ of tooth movement S, while angle $\phi$ of vector S relative to force K occurring on the real axis described the lag of tooth movement S behind force K. In the same manner as through amplitude $A_S$ and angle $\phi$, vector S can also be characterized by real component $S_r$ and imaginary component $S_i$, whose geometric sum represents vector S.

With a given force amplitude, tooth deflection amplitude $A_S$ as well as phase shift $\phi$ between periodic force and periodic tooth deflection depend upon the frequency of the force. The higher the frequency, the smaller the deflection amplitude of the tooth, however the faster the tooth movement will follow the force, i.e., phase angle $\phi$. With a frequency of 0, i.e., for an infinitely slow increase in force, the tooth deflection will follow the force without any lag, i.e., without phase shifting, while tooth deflection amplitude $A_S$ will be at a maximum relative to finite force frequencies. For this reason, point N in FIG. 8 represents the peak of the vector. As the frequency of force K increases with a constant force amplitude, the peaks of vectors S describe curve 136, which is also termed a frequency hodograph of the tooth movement, in the direction of arrow 137 to point O, which corresponds to an infinitely high frequency.

On the frequency hodograph of FIG. 8, that frequency at which the amplitude of vector S is half as large as the maximum amplitude at frequency O (point N) is stipulated as the standard or reference value. This is the case at point P. The frequency so defined is termed the limit frequency $fg$. The frequency hodograph of the tooth movement is standardized by using the ratio $f/fg$, i.e., multiples or fractions of limit frequency $fg$, as the parameter of the hodograph.

Important information can undoubtedly be obtained from vector S of the tooth movement with constant force amplitude and variable force frequency as well as with constant force frequency and variable force amplitude. The one provides information about so-called relaxation or after-effect situations, the other permits any nonlinearities in the force/distance curve to be noticed.

Figure 9:
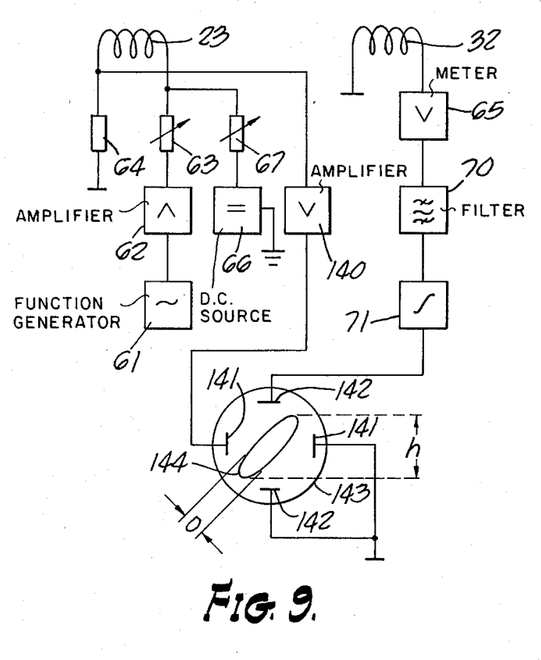
FIG. 9 depicts a modified circuit schematic diagram.
Figures 10, 11A:
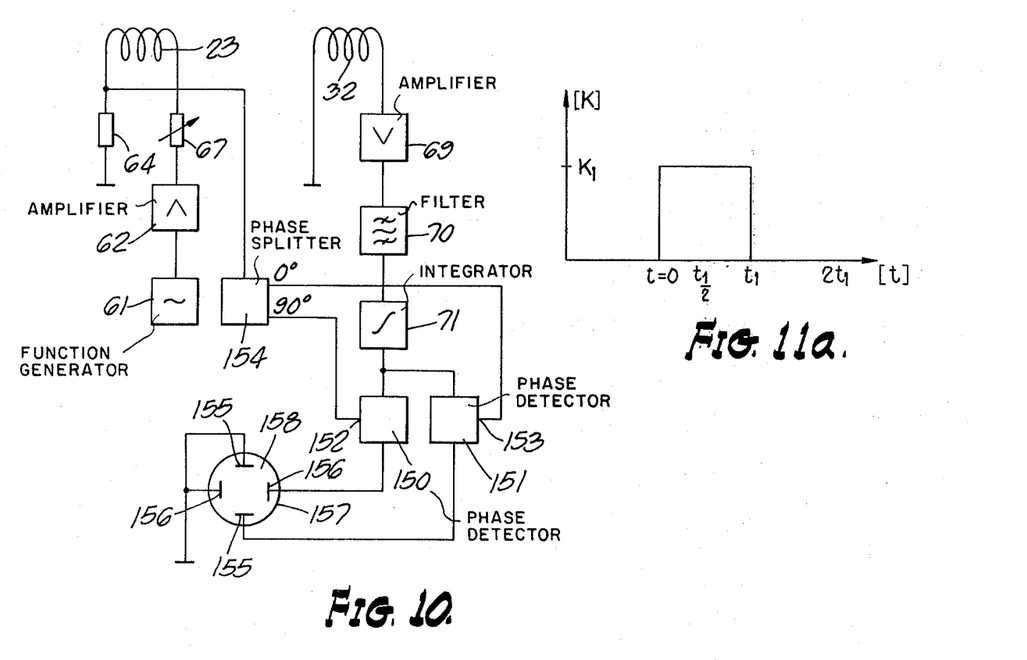
FIG. 10 shows a further circuit schematic.
FIGS. 11a and 11b are graphs of the variation of a force and a movement in time.

Modifications of the circuit arrangement of FIG. 4 are illustrated in FIGS. 9 and 10 for determining the parameters characterizing vector S of the tooth movement, i.e., amplitude $A_S$ and phase angle $\phi$, as well as components $S_r$ and $S_i$. In these figures, those elements which are identical with elements in the previous circuit are numbered with the same reference numerals. FIG. 9 shows an arrangement in which the voltage at resistor 64, which is proportional to the force coil current and thus to periodic alternating force K, is amplified by amplifier 140 and supplied to the horizontal deflection plates 141 of a cathode-ray tube 143, while the output voltage at integrator 71 is applied to its vertical deflection plates 142. Using the ellipses appearing on the screen of cathode-ray tube 143, the vertical deflection h is employed as a dimension for the amplitude of tooth movement S, and opening $o$ as the dimension of phase angle $\phi$.

The arrangement according to FIG. 10 offers the possibility of immediate display of the complex tooth movement plane on a screen. This is accomplished by supplying the output voltage of integrator 71 to two phase detectors 150 and 151, whose control voltage at inputs 152 and 153 is obtained as described below. In the phase splitter 154, the voltage at resistor 64, which is proportional to the force coil current, is split into a first control voltage with a phase difference of 0° to the input voltage of the phase splitter, and into a second control voltage with a phase difference of 90° to the input voltage of the phase splitter. Thus, D. C. voltages are formed at the outputs of phase detectors 150, 151, the first D. C. voltage being proportional to the real portion of the output voltage of integrator 71 and the second being proportional to the imaginary portion of the output voltages of the integrator. These D. C. voltages are applied to the pair of vertical deflection plates 155 and the pair of horizontal deflection plates 156 of the cathode-ray tube 157. In this manner, the point 158 appearing on the screen is deflected from its original position in the center of the picture in such a manner that its position corresponds directly to the peak of vector S of the tooth movement. In this connection, the voltage at the vertical pair of deflection plates 155 is proportionate to the real component $S_r$ of vector S, while the voltage on the horizontal pair of deflection plates 156 is proportionate to the imaginary component $S_i$ of vector S.

Further important information can be obtained by superimposing a smaller periodic force over a static application of force to the tooth. If, for example, the static force is increased in a linear manner as a factor of time as in Hofmann's periodontograms by increasing the current from D. C. supply 66 in a linear manner as a factor of time according to FIG. 9, while simultaneously supplying a smaller A. C. supply to coil 23 from amplifier 62, the phase and amplitude of the periodic tooth movement which superimposes the static deflection, provides especially important additional information for the quasi-static periodontogram. The largely different movement mechanism of phase I (primarily friction) and of phase II (primarily elastic tension) of the tooth movement provides, in the case of a superposition of this type of a small periodic force over the static force which is increasing in a linear manner as a factor of time, measurements which differ extremely in phases I and II in terms of both amplitude and phase angle.

While a fixed point on the test subject was not required during the above described examinations with a primarily periodic force and the employment of a transducer head suspension system according to FIG. 5, it shall now be shown that the transducer system according to the present invention also provides significant advantages if quasi-static examinations of the tooth movement according to Hofmann's periodontograms are to be performed in which the transducer head is supported and suspended according to FIGS. 6 and 7. While the linear increase as a factor of time selected by Hofmann was achieved with mechanical means, by employing electronic function generators with the present transducer system, it is easy to bring about a number of other force curves, whose resulting displacement curve should provide increased information regarding the functional condition of the periodontium. This will be explained on the basis of two examples, one dealing with a force curve in the form of one force jump, the other with a step-like force curve.

In the first example, at time $t = 0$ the force quickly jumps from a value of 0 to a selectable amount $K_1$, and, after a preselectable time $t = t_1$, jumps back to the value $K = 0$, in accordance with FIG. 11a.

Figure 11B:
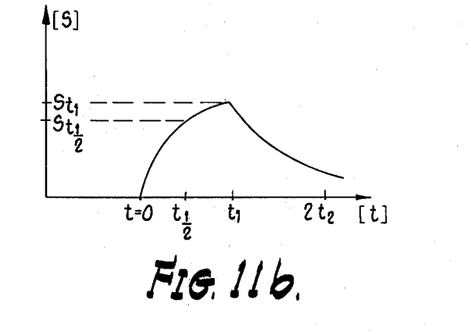

During initial phase I, where the occurrences are mainly of a frictional nature, tooth deflection S as a factor of time $t$ results in a curve according to FIG. 11b, which is defined by the following equation:

$$S_t = S_{t\infty}(1 - e^{-\delta_B \cdot t}) \tag{6}$$

In the above, $S_t$ is the tooth deflection at time $t$, while $S_{t\infty}$ is the state of equilibrium of the tooth deflection after the force has been applied for a very long time, i.e., the maximum tooth deflection. The constant $\delta$ is definitive for the rapidity with which the tooth displacement follows the force. A large $\delta$ value represents rapid adaptation of the tooth to the equilibrium of maximum tooth deflection. Index B on constant $\delta$ in equation (6) means that constant $\delta$ applies for the condition under load. After the force is switched off at time $t = t_1$, the return sequence occurs, which can be described by equation (7):

$$S_t = S_{t_1} \cdot e^{-\delta_U(t-t_1)} \tag{7}$$

Index U on constant $\delta$ characterizes the no-load condition.

Hofmann has already pointed out that the load period plays a significant role, especially with forces of up to 200 grams. In addition, Hofmann also says that with 150 grams and load periods of between 0.6 and 1.2 seconds, the measurements of the tooth deflection on the same tooth can differ by up to 50%.

The curve of the tooth deflection after a sudden force increase to a defined value undoubtedly provides a greater information content than with a force increase which is linear as a factor of time, as in this case the result depends upon the specially selected velocity of force increase. This can clearly be seen from FIG. 1, where the steepness of the displacement curve, with which the force would have to differ much less during initial phase I and periodontal phase II than would be necessary to correspond to the basically different mechanisms in phases I and II, upon which the tooth deflection is based. Only through the velocity of force increase of 120 grams in 3.2 seconds selected in FIG. 1 do the two slopes of the distance curve in phases I and II come so close together. With a force increase that is ten times slower, for example, the slope of the increase of tooth deflection S with force K, i.e., dS/dK, would increase significantly in phase I, while dS/dK would remain largely unchanged in phase II.

From the diagram according to FIG. 11b and equations (6) and (7), it is possible to see four important absolute parameters for the functional condition of the periodontium, which will be derived below.

If the tooth deflections at time $t = \frac{1}{2}t_1$ and $t = t_1$ are designated $S_{t_1}$ and $S_{t_1}$ and the quotient of the above tooth deflection as $Q_{S_B}$, then $$Q_{S_B} = (S_{t_1})/(S_{t_1}) \tag{8}$$

and if these values are used in equation (6), equation (9) results, which provides $\delta_B$:

$$\delta_B \cdot t_1 = 2 \ln (Q_{S_B})(1 - Q_{S_B}) \tag{9}$$

Thus, with a given load time $t_1$, it is only necessary to determine the tooth deflections at time $t_1$ and at time $\frac{1}{2}t_1$ in order to be able to calculate the important parameter $\delta_B$, which characterizes the movement while the tooth is subjected to a load, from equation (9).

The second of the above mentioned parameters is the relaxation time for the load sequence $T_{relax\,B}$, which will be defined as the time prior to achieving a deflection $S_{relax}$ of 90% of the maximum possible deflection $S_{t\infty}$. By inserting $S_{relax}/S_t = 0.9$ in equation (6) we find:

$$T_{relax} = (\ln 10/\delta_B) = (2.303/\delta_B) \tag{10}$$

In a similar manner, parameter $\delta_u$ can also be determined for the relief sequence of the tooth if the tooth deflections for time $t_1$ and $2\,t_1$, i.e., $S_{t_1}$ and $S_{2t_1}$, as well as the quotient of these tooth deflections, i.e., $$Q_{S_U} = S_{2t_1}/S_{t_1}$$

(11)

are inserted in equation (7):

$$\delta_u \cdot t_1 = \ln Q_{S_u} \tag{12}$$

The fourth of the above mentioned parameters, the relaxation time for the relief sequence $T_{relax_u}$, will be defined as the time prior to return of deflection $S_{t_1}$ at time $t_1$ to a value $S_{2t_1}$, which is 90% smaller, at time $2t_1$. By inserting $(S_{2t_1}/S_{t_1}) = 0.1$ in equation (7), we find:

$$T_{relax_u} = \ln 10/\delta_u + 2.303/\delta_u \tag{13}$$

In the case of small return velocities of the relieved tooth, it can be practical to employ a greater period than $2\,t_1$ for defining the relaxation time.

As the second of the two above mentioned examples, we shall now consider a case in which the maximum tooth deflection is achieved by means of a step-like increase in force to its maximum value instead of one jump in force. By correspondingly reducing the force in a step-like manner, it is then possible to return the force to its initial value of zero again. This can be achieved, for example, in ten upward steps of 3 seconds each until a final value of 120 grams force has been reached, followed by ten downward force jumps, with the force being kept constant throughout the duration of each step.

As indicated above, in treating the tooth movement with only one force step, it is possible to gain important physiological parameters, such as parameters $\delta_B$ and $\delta_U$, in which frictional sequences are determined quantitatively, as well as relaxation time $T_{relax_B}$ and $T_{relax_U}$.

If the tooth movement sequence is registered with step-like upward and downward force stages, the corresponding parameters, which represent the physiological and pathological condition of the periodontium, will be distributed throughout the entire initial and periodontal phase with a plurality of load and relief stages.

To make evaluation of tooth movement sequences of this nature as a factor of time more efficient, it is possible to employ a small computer which prints the respective $\delta$ and $T_{relax}$ values over the corresponding positive and negative force stages, so that the printed result can be obtained immediately after the force steps have been completed.

In closing, mention should again be made of Hofmann's finding, which states that the jumps occurring periodically with the systole during phase IV of the periodontograms should be considered a common, significant parameter of all periodontium diseases studied by him, and thus as early symptoms of an inflammatory alteration of the periodontium.

In the case of oral force, the systole pressure opposes the deflecting force, while it accelerates the return. In the case of a tooth pressed tightly against the compressed tissue wall, this return is greatest during the first systole after the force is switched off. If force pulses with a duration which is equal to the time between two pulse beats are applied by the force generator, followed by one pulse period where force $K = 0$, the phase point of the first systole can be shifted to the moment after force is removed from the tooth (return) when the greatest return step occurs after the force is switched off as a result of the first systole.

Switching the force of the force generator on and off over one or a plurality of pulse lengths to form a constant force can be controlled by the pulse itself, by taking the control pulses with a photo-electric pulse counter attached to the ear lobe in order to be able to switch off the force from the force generator at that moment in which the first systole results in the greatest return effect of the tooth.

Moreover, the method can be made even more precise by not writing the return displacement, but taking the electrical voltage in front of the integrator and then amplifying it, which causes the return movement of the tooth caused by the first systole after the force is relieved to be represented as an electrical pulse. This pulse is then supplied to a capacitor, which converts the magnitude of the electrical pulse to a meter deflection as a disgnostic parameter.

I claim:

1. Apparatus for examining the human periodontium in which a force acts on the tooth to be examined and the movement of the tooth resulting from the force is determined, the force being transmitted to the tooth by a rigid tube medium sliding in a transducer head and the deflection of the tooth is measured, comprising:
   a conductor through which current flows;
   a means for producing magnetic flux passing through the conductor at right angles;
   a source of supply of electric current connected to the conductor such that the flux density of the magnetic flux is constant within a certain area in the direction in which the resultant force acts between the rigid medium and the transducer head; and
   a dynamic displacement pickup installed in the transducer head including a coil connected to the tube and a permanent magnetic circuit having an air gap in which said coil is movably located, and said dynamic displacement pickup is carried by the transducer head and generates an electric signal proportional to the deflection of the tube from a predetermined position, the electric signal from the dynamic displacement pickup being connected to follower means through an amplifier, and the follower means drivingly connected with the transducer head to move the same until the coil is centrally located in the constant area of the magnetic flux in the air gap.

2. Apparatus as in claim 1, in which the electrical conductor is formed into a coil carried by the rigid medium and the magnetic flux is generated in an air gap of a magnetic circuit incorporated in the transducer head.

3. Apparatus as in claim 2, in which the length of the area of constant magnetic flux in the air gap is greater than the length of the coil.

4. Apparatus as in claim 2, in which the air gap has the shape of a ring in which the lines of force of magnetic flux extend radially and within which the coil is arranged coaxially, and the rigid medium includes a tube to which the coil is attached by means of a frame, said tube being movably arranged in an opening through elements of the magnetic circuit located on the center axis of the air gap and the coil.

5. Apparatus as in claim 2, in which the air gap is ring-shaped with the coil coaxially located therein such that the lines of magnetic flux generated by said coil extend radially; and the rigid medium includes a tube connected to the coil for movement therewith, said tube being journaled in an opening in certain elements of the magnetic circuit via thrust bearings.

6. Apparatus as in claim 2, in which the air gap is ring-shaped with the coil coaxially located therein, such that the lines of magnetic flux generated by said coil extend radially; and the rigid medium includes a tube connected to the coil for movement therewith.

7. Apparatus as in claim 1, in which there is further provided a displacement pickup connected to the rigid medium and through which the force is applied to the tooth.

8. Apparatus as in claim 1, in which the voltage from the coil is fed into electrical integrating means prior to being evaluated.

9. Apparatus as in claim 1, in which the coil is interconnected with a frequency selective filter prior to being evaluated.

10. Apparatus as in claim 1, in which the static displacement pickup is carried by the transducer head and generates an electric signal proportional to the deflection of the tube from a predetermined position.

11. Apparatus as in claim 1, in which the static displacement pickup is carried by the transducer head and generates an electrical signal proportional to the deflection of the tube from the central position of the coil in the constant area of magnetic flux in the air gap.

12. Apparatus as in claim 1, in which the source of supply of current to the force generator includes a sine-wave oscillator and a D. C. generator, the current output of said oscillator and D. C. generator being superimposed.

13. Apparatus as in claim 1, in which the source of supply of current to the force generator includes a function generator and a D. C. generator, the current outputs of said function generator and said D. C. generator being superimposed.

14. Apparatus for examining the human periodontium in which a force acts on the tooth to be examined and the movement of the tooth resulting from the force is determined, the force being transmitted to the tooth by a rigid tube medium sliding in a transducer head and the deflection of the tooth is measured, comprising:

a conductor through which current flows;

a means for producing magnetic flux passing through the conductor at right angles;

a source of supply of electric current connected to the conductor such that the flux density of the magnetic flux is constant within a certain area in the direction in which the resultant force acts between the rigid medium and the transducer head; and a dynamic displacement pickup installed in the transducer head including a coil connected to the tube and a permanent magnetic circuit having an air gap in which said coil is movably located, and in which the pickup coil is interconnected with a filter and integrator serially arranged, the integrator output being fed to a first pair of deflection plates of a cathode-ray tube; and an electric signal proportional to the sinusoidal current through the force coil is connected to a second pair of deflection plates of the cathode-ray tube.

15. Apparatus for examining the human periodontium in which a force acts on the tooth to be examined and the movement of the tooth resulting from the force is determined, the force being transmitted to the tooth by a rigid tube medium sliding in a transducer head and the deflection of the tooth is measured, comprising:

a conductor through which current flows;

a means for producing magnetic flux passing through the conductor at right angles;

a source of supply of electric current connected to the conductor such that the flux density of the magnetic flux is constant within a certain area in the direction in which the resultant force acts between the rigid medium and the transducer head; and a dynamic displacement pickup installed in the head; and transducer head including a coil connected to the tube and a permanent magnetic circuit having an air gap in which said coil is movably located, in which the pickup coil is connected in series with a filter, an integrator and a phase detector, said detector having a control input including the sinusoidal current from the force coil.

16. Apparatus for examining the human periodontium in which a force acts on the tooth to be examined and the movement of the tooth resulting from the force is determined, the force being transmitted to the tooth by a rigid tube medium sliding in a transducer head and the deflection of the tooth is measured, comprising:

a conductor through which current flows;

a means for producing magnetic flux passing through the conductor at right angles;

a source of supply of electric current connected to the conductor such that the flux density of the magnetic flux is constant within a certain area in the direction in which the resultant force acts between the rigid medium and the transducer head; and a dynamic displacement pickup installed in the transducer head including a coil connected to the tube and a permanent magnetic circuit having an air gap in which said coil is movably located, in which the pickup coil is serially interconnected, in the order stated, with a filter, and an integrator, the output of the integrator is supplied to both first and second phase detectors, the control inputs for said phase detectors being two electrical signals taken from the sinusoidal current through the force coil and having a respective phase relationship of 90°.

17. Apparatus for examining the human periodontium in which a force acts on the tooth to be examined and the movement of the tooth resulting from the force is determined, the force being transmitted to the tooth by a rigid tube medium sliding in a transducer head and the deflection of the tooth is measured, comprising:

a conductor through which current flows;

a means for producing magnetic flux passing through the conductor at right angles;

a source of supply of electric current connected to the conductor such that the flux density of the magnetic flux is constant within a certain area in the direction in which the resultant force acts between the rigid medium and the transducer head; and a dynamic displacement pickup installed in the transducer head including a coil connected to the tube and a permanent magnetic circuit having an air gap in which said coil is movably located, in which the pickup coil is serially interconnected, in the order stated, with a filter and an integrator, the output of the integrator is supplied to both first and second phase detectors, the control inputs for said phase signals taken from the sinusoidal current in the force coil and having a respective phase relationship of 90-degrees; the output of the first phase detector is applied to a pair of deflection plates of a cathode-ray tube, and the output voltage of the second phase detector is applied to the other pair of deflection plates of the cathode-ray tube.

18. Apparatus for examining the human periodontium in which a force acts on the tooth to be examined and the movement of the tooth resulting from the force is determined, the force being transmitted to the tooth by a rigid tube medium sliding in a transducer head and the deflection of the tooth is measured, comprising:

a conductor through which current flows;

a means for producing magnetic flux passing through the conductor at right angles;

a source of supply of electric current connected to the conductor such that the flux density of the magnetic flux is constant within a certain area in the direction in which the resultant force acts between the rigid medium and the transducer head;

a dynamic displacement pickup installed in the transducer head including a coil connected to the tube and a permanent magnetic circuit having an air gap in which said coil is movably located; and a cap of a ferromagnetic material open at the sides is attached to the crown of the tooth to be examined and a magnet attached to the end of the tube temporarily connects the tube with the tooth during the examination.

* * * * *

UNITED STATES PATENT OFFICE
CERTIFICATE OF CORRECTION

Patent No. 4,058,115          Dated November 15, 1977

Inventor(s) FRIEDRICH M. O. FÖRSTER

It is certified that error appears in the above-identified patent and that said Letters Patent are hereby corrected as shown below:

[30]     Foreign Application Priority Data

Nov. 6, 1974     Germany     2452578

Column 5, line 59, delete "froce" and insert --force--.

Column 9, line 40, delete "perfrom" and insert --perform--.

Signed and Sealed this

Fourth Day of April 1978

[SEAL]

Attest:

RUTH C. MASON
Attesting Officer

LUTRELLE F. PARKER
Acting Commissioner of Patents and Trademarks